(12) United States Patent
Abrams et al.

(10) Patent No.: US 7,517,357 B2
(45) Date of Patent: Apr. 14, 2009

(54) KNOTLESS SUTURE ANCHOR

(75) Inventors: Jeffery Abrams, Princeton, NJ (US);
William Reimels, Blue Bell, PA (US);
Chris Keegan, Hatboro, PA (US)

(73) Assignee: Linvatec Biomaterials, Tampere (FI)

( * ) Notice: Subject to any disclaimer, the term of this patent is extended or adjusted under 35 U.S.C. 154(b) by 265 days.

(21) Appl. No.: 10/338,687

(22) Filed: Jan. 9, 2003

(65) Prior Publication Data

US 2004/0138706 A1    Jul. 15, 2004

(51) Int. Cl.
*A61B 17/04* (2006.01)
(52) U.S. Cl. .................. 606/232; 606/300; 606/318
(58) Field of Classification Search ............... 606/232, 606/72, 73, 300–319
See application file for complete search history.

(56) References Cited

U.S. PATENT DOCUMENTS

| | | | | |
|---|---|---|---|---|
| 4,750,492 A | * | 6/1988 | Jacobs | 606/230 |
| 4,870,957 A | * | 10/1989 | Goble et al. | 606/73 |
| 4,968,317 A | | 11/1990 | Tormala et al. | |
| 5,268,001 A | | 12/1993 | Nicholson et al. | |
| 5,336,240 A | | 8/1994 | Metzler et al. | |
| 5,370,662 A | * | 12/1994 | Stone et al. | 606/232 |
| 5,383,905 A | * | 1/1995 | Golds et al. | 606/232 |
| 5,423,860 A | * | 6/1995 | Lizardi et al. | 606/232 |
| 5,464,427 A | * | 11/1995 | Curtis et al. | 606/232 |
| 5,480,403 A | * | 1/1996 | Lee et al. | 606/72 |
| 5,486,197 A | * | 1/1996 | Le et al. | 606/232 |
| 5,527,342 A | * | 6/1996 | Pietrzak et al. | 606/232 |
| 5,545,180 A | * | 8/1996 | Le et al. | 606/232 |
| 5,569,269 A | | 10/1996 | Hart et al. | |
| 5,584,835 A | * | 12/1996 | Greenfield | 606/73 |
| 5,630,824 A | * | 5/1997 | Hart | 606/139 |
| 5,643,321 A | | 7/1997 | McDevitt | |
| 5,649,963 A | | 7/1997 | McDevitt | |
| 5,702,397 A | * | 12/1997 | Goble et al. | 606/72 |
| 5,720,765 A | * | 2/1998 | Thal | 606/232 |
| 5,723,013 A | * | 3/1998 | Jeanson et al. | 623/17.16 |
| 5,725,529 A | * | 3/1998 | Nicholson et al. | 606/72 |
| 5,911,721 A | * | 6/1999 | Nicholson et al. | 606/72 |
| RE36,289 E | * | 8/1999 | Le et al. | 606/232 |
| 5,935,129 A | | 8/1999 | McDevitt et al. | |
| 5,948,000 A | * | 9/1999 | Larsen et al. | 606/232 |
| 5,948,001 A | | 9/1999 | Larsen | |
| 5,957,953 A | * | 9/1999 | DiPoto et al. | 606/232 |
| 5,980,558 A | | 11/1999 | Wiley | |
| 6,024,758 A | | 2/2000 | Thal | |
| 6,045,574 A | | 4/2000 | Thal | |

(Continued)

FOREIGN PATENT DOCUMENTS

EP    1 013 229    6/2000

(Continued)

OTHER PUBLICATIONS

International Search Report for PCT/US04/00043.

*Primary Examiner*—Darwin P Erezo
(74) *Attorney, Agent, or Firm*—Kenyon & Kenyon LLP

(57) ABSTRACT

A suture anchor that allows a surgeon to securely and efficiently suture soft tissue to bone without knotting the suture, comprising a locking body through which a suture is passed, and an anchor collar, which, when positioned over the suture passing through the locking body, secures the suture.

4 Claims, 9 Drawing Sheets

U.S. PATENT DOCUMENTS

| | | | |
|---|---|---|---|
| 6,086,608 A * | 7/2000 | Ek et al. | 606/232 |
| 6,200,329 B1 * | 3/2001 | Fung et al. | 606/232 |
| 6,319,271 B1 * | 11/2001 | Schwartz et al. | 606/232 |
| 6,406,498 B1 | 6/2002 | Tormala et al. | |
| RE37,963 E * | 1/2003 | Thal | 606/232 |
| 6,520,980 B1 * | 2/2003 | Foerster | 606/232 |
| 6,533,816 B2 * | 3/2003 | Sklar | 623/13.14 |
| 6,585,730 B1 * | 7/2003 | Foerster | 606/32 |
| 6,652,563 B2 * | 11/2003 | Dreyfuss | 606/232 |
| 6,692,516 B2 * | 2/2004 | West et al. | 606/232 |
| 6,736,829 B1 * | 5/2004 | Li et al. | 606/232 |
| 6,840,953 B2 * | 1/2005 | Martinek | 606/232 |
| 7,090,690 B2 * | 8/2006 | Foerster et al. | 606/232 |
| 2002/0095180 A1 | 7/2002 | West, Jr. et al. | |
| 2002/0147463 A1 * | 10/2002 | Martinek | 606/232 |
| 2003/0065361 A1 * | 4/2003 | Dreyfuss | 606/232 |
| 2003/0195563 A1 * | 10/2003 | Foerster | 606/232 |
| 2004/0138706 A1 * | 7/2004 | Abrams et al. | 606/232 |

FOREIGN PATENT DOCUMENTS

| | | |
|---|---|---|
| WO | WO 01/10312 | 2/2001 |
| WO | WO 02/17795 | 3/2002 |
| WO | WO 02/051325 | 7/2002 |

\* cited by examiner

KNOTLESS SUTURE ANCHOR

FIELD OF THE INVENTION

This invention relates to the field of suture anchors used to attach soft tissue to bone. More particularly, this invention relates to a knotless suture anchor.

BACKGROUND OF THE INVENTION

Often, doctors have to attach various soft tissues, such as tendons and ligaments, to hard tissue, such as bone. To provide an alternative to suturing the soft tissue directly through tunnels in the bone, suture anchors have been developed to aid in this attachment. Generally, the doctor will attach such soft tissue to bone by suturing the soft tissue to a suture anchor that has been placed in the bone. During this suturing procedure, the surgeon must pass a suture through the tissue to be repaired, attach it to the suture anchor, and knot the suture so that the tissue is securely fastened to the suture anchor. Knotting a suture, particularly when operating within a joint arthroscopically, requires great skill on the part of the surgeon and can be extremely time consuming. Further, knots in sutures can be bulky, and cause irritation or damage within a joint. Thus, there is a desire to develop a suture anchor that may effectively, efficiently, and securely attach soft tissue to bone without requiring the surgeon to knot the suture.

One attempt to develop a knotless suture anchor resulted in a suture anchor that has a loop of suture thread pre-tied to the suture anchor. In order to affix soft tissue to bone using this suture anchor, the surgeon must pass the loop through the soft tissue and then pass the suture anchor back through the loop. This technique is difficult to perform, particularly arthroscopically, and also is time consuming.

In addition, suture anchors that have loops of suture already attached to them suffer from several other drawbacks. For instance, the surgeon must use the type and length of suture that comes pre-attached to the suture anchor. However, different applications may require different types and lengths of suture. It is preferable for a surgeon to be able to use whatever suture he feels is appropriate for a particular application.

Further, the techniques with which the surgeon may suture the soft tissue are limited when using a loop of suture thread of predetermined length that is already attached to the suture anchor. It is more preferable to give the surgeon the freedom to attach the suture to the soft tissue in whichever manner he desires, depending upon the particular application.

Thus, there is a need for a suture anchor that may be used efficiently and easily, without requiring the surgeon to tie a knot, yet allowing the surgeon maximum flexibility in the manner in which he attaches the suture to the soft tissue.

SUMMARY OF THE INVENTION

In a preferred embodiment, the suture anchor of the present invention comprises a locking body containing an opening, or eyelet, for receiving suture thread, and a collar that is capable of moving along the locking body. At the distal end of the locking body there is a head for securing the locking body into the bone. The head allows the locking body to be inserted into the bone, put prevents the body from easily being pulled out of the bone. Similarly, the collar is designed so that it may be inserted into bone, but may not easily be pulled out of the bone. The suture anchor may be made of biostable or biodegradable material. In a preferred embodiment, the suture anchor is made of strong, self-reinforced, bioabsorbable polymer.

In an embodiment of the present invention, a suture anchor is provided, comprising a locking body including a shaft, an eyelet configured to receive one or more suture threads, and at least one protuberance for securing the central anchoring post in bone and a collar movably engaged with the central anchoring post, the collar having a hole there through and having an exterior surface comprising at least one protuberance for securing the collar in bone, where the collar is configured to secure one or more suture threads between the collar and the locking body.

Another embodiment of the present invention provides a method for attaching tissue to bone. The method includes, providing a suture anchor as described above, attaching suture thread to the tissue, positioning the ends of the suture through the eyelet, with the collar located distally to the eyelet, inserting the suture anchor into a pre-drilled hole in the bone while keeping the collar positioned distally to the eyelet, positioning the tissue by applying force to the ends of the suture, and further inserting the locking body into the hole in the bone so that the collar is located proximally to the eyelet, with the suture threads secured between the collar and the central anchoring post.

DETAILED DESCRIPTION

Figure 1:
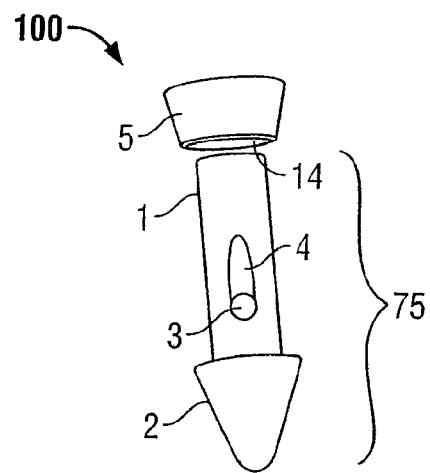
FIG. 1 shows a perspective view of an embodiment of the suture anchor of the present invention, including the locking body and collar.

The present invention provides a suture anchor that allows a surgeon to securely suture soft tissue to bone without having to knot the suture. FIGS. 1 and 2a-c show preferred embodiments of the present invention. In these Figures, the suture anchor 100 of the present invention comprises a locking body 75 and an anchor collar 5. The locking body 75 includes a central anchoring post 1 and distal head 2. The anchor collar 5 is designed so that it may move relative to the locking body 75. In a preferred embodiment, the anchoring collar 5 slides over the locking body 75, which acts as a locking mechanism after insertion.

The distal head 2 of locking body 75 is designed so that the locking body 75 may be inserted into bone, but may not easily be pulled out of the bone. The distal head 2 of the suture anchor 100 has a wedge shape, however other shapes may be used, provided that they do not allow the locking body 75 to be easily pulled out of bone after insertion. For example, distal head 2 may have ridges, protrusions, spikes, scales, or screw threads.

The locking body 75 also includes an eyelet 3 for receiving suture thread. The eyelet 3 may be designed so as to receive one or more suture threads. This allows the soft tissue to be more securely fastened to the bone, and reduces the likelihood of suture wear or breakage, which may result in an ineffective repair.

In a preferred embodiment, the locking body 75 may also comprise one or more indentations 4 located proximal to the eyelet 3 for receiving suture thread. The indentations 4 provide a guide for the suture thread, thereby reducing the movement of the suture during insertion of the suture anchor 100. Further, the indentations 4 allow the suture collar 5 to more easily pass over the suture that is threaded through eyelet 3, and more gradually engage the suture, thereby reducing the risk of suture wear or breakage, which may result in an ineffective repair.

The locking body 75 may also comprise means 3a for preventing the anchor collar 5 from being separated from the proximal end of the locking body 75. In a preferred embodiment, these means 3a are a section of the locking body 75, which at its proximal end is wider in cross section than the inner diameter 14 of the anchor collar 5, thereby locking the anchor collar 5 after insertion.

The anchor collar 5 is designed to be able to be pushed in the distal direction into bone, but not easily pulled out of the bone. The outer surface of the anchor collar 5 has a wedge shape, however other shapes may be used, provided that they do not allow the anchor collar 5 to be easily pulled out of bone after insertion. For example, the collar may include ridges, spikes, scales, or the like.

Figure 2A:
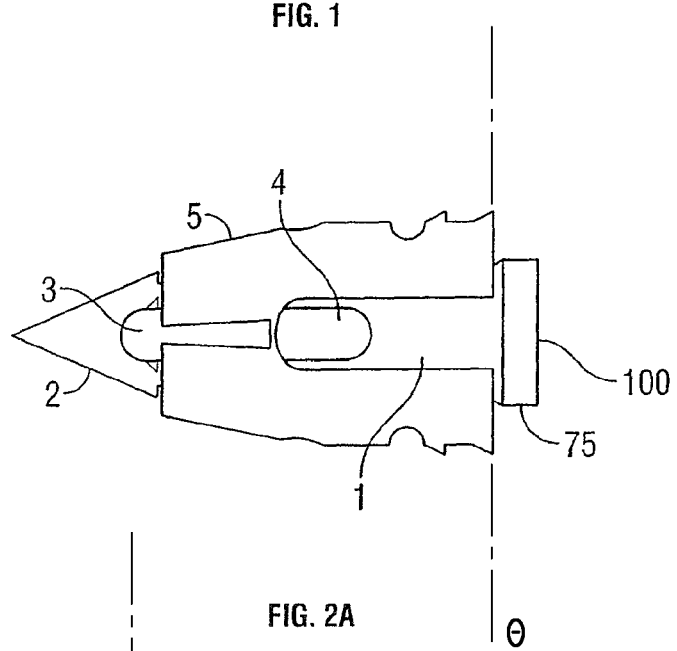
FIGS. 2a-2c show perspective views of an embodiment of the present invention including the locking body and collar of a suture anchor.
Figure 2B:
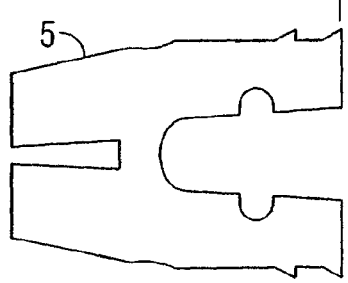
Figure 2C:
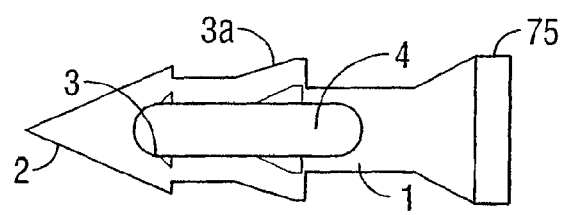

The anchor collar 5 has an initial diameter θ at its proximal end as shown in FIGS. 2a and 2b. In a preferred embodiment, the initial diameter θ is equal to or greater than 4 mm. This diameter will change upon final installation of the suture anchor 100.

The suture anchor may be constructed of biostable or biodegradable materials that are known to those of skill in the art. Table 1 includes a number of these materials.

TABLE 1

Biodegradable Polymers

Polyglycolide (PGA)Glycolide copolymers
Glycolide/lactide copolymers (PGA/PLA)
Glycolide/trimethylene carbonate copolymers (PGA/TMC)
Stereoisomers and copolymers of PLA
Poly-L-lactide (PLLA)
Poly-D-lactide (PDLA)
Poly-DL-lactide (PDLLA)
L-lactide/DL-lactide copolymersL-lactide/D-lactide copolymers
Copolymers of PLA
Lactide/tetramethylene glycolide copolymers
Lactide/trimethylene carbonate copolymers
Lactide/δ-valerolactone copolymers
Lactide/ε-caprolactone copolymers
Polydepsipeptides (glycine-DL-lactide copolymer)
PLA/ethylene oxide copolymers
Asymmetrically 3,6-substituted poly-1,4-dioxane-2,4-diones
Poly-β-hydroxybutyrate (PHBA)
PHBA/β-hydroxyvalerate copolymers (PHBA/PHVA)
Poly-β-hydoxypropionate (PHPA)
Poly-β-dioxanone (PDS)
Poly-δ-valerolactone
Poly-ε-caprolactone
Methylmethacrylate-N-vinylpyrrolidone copolymers
Polyesteramides
Polyesters of oxalic acid
Polydihydropyranes
Polyalkyl-2-cyanoacrylates
Polyurethanes (PU)
Polyvinyl alcohol (PVA)
Polypeptides
Poly-β-maleic acid (PMLA)
Poly-β-alkanoic acids
Polyethylene oxide (PEO)
Chitin polymers In a preferred embodiment, the suture anchor may be constructed of self-reinforced biodegradable polymer, such as is disclosed in U.S. Pat. Nos. 6,406,498 and 4,968,317, which are hereby incorporated by reference. In another preferred embodiment, the locking body 1 and the anchor collar 5 are formed from different materials. For example, the locking body 1 may be constructed from self-reinforced biodegradable polymer and the anchor collar 5 may be formed from non self-reinforced biodegradable polymer.

Figure 3:
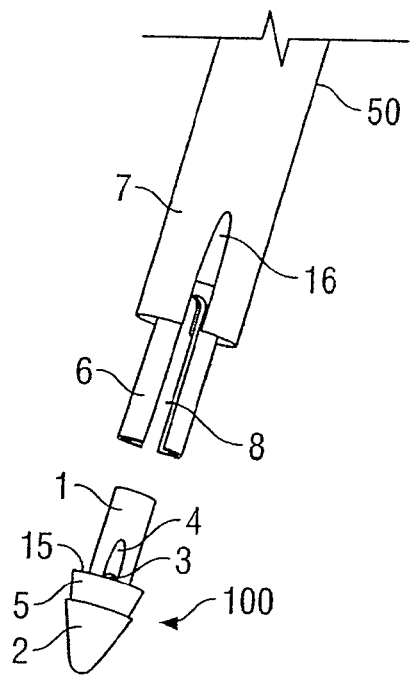
FIG. 3 shows a perspective view of an embodiment of the suture anchor of the present invention and an installation instrument for inserting the suture anchor.

FIG. 3 shows that the anchor collar 5 may be positioned distally on the locking body 75 with respect to the eyelet 3. FIG. 3 also shows a preferred embodiment of an installation tool 50 used to install the suture anchor 100. The installation tool 50 comprises a cannula 7, an anchor collar holder 6, and a push rod 35 (not shown). Anchor collar holder 6 is designed to hold anchor collar 5 while push rod 35 pushes the locking body 75 into bone. The anchor collar holder 6 has a central indentation for receiving the proximal end of the locking body 75. The distal end of the anchor collar holder 6 contacts the proximal end of the anchor collar 5. When force is applied to the push rod 6, both the anchor collar 5 and the locking body 75 may be pushed into bone. In a preferred embodiment, the anchor collar holder 6 may have a gap 8 for allowing a suture to more freely pass through the eyelet 3. Likewise, the cannula 7 may have a gap 16 for allowing a suture to more freely pass through the eyelet 3. The insertion tool 50 of FIG. 3 allows the suture anchor 100 to be easily and quickly inserted into a bone in an arthroscopic procedure.

Figure 4:
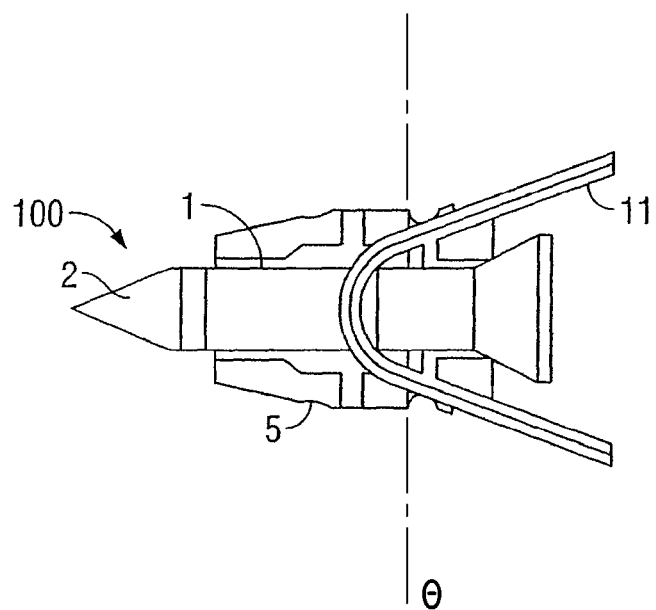
FIG. 4 shows a cross section view of an embodiment of the present invention including an initial configuration of the locking body, collar, and a suture.
Figure 5:
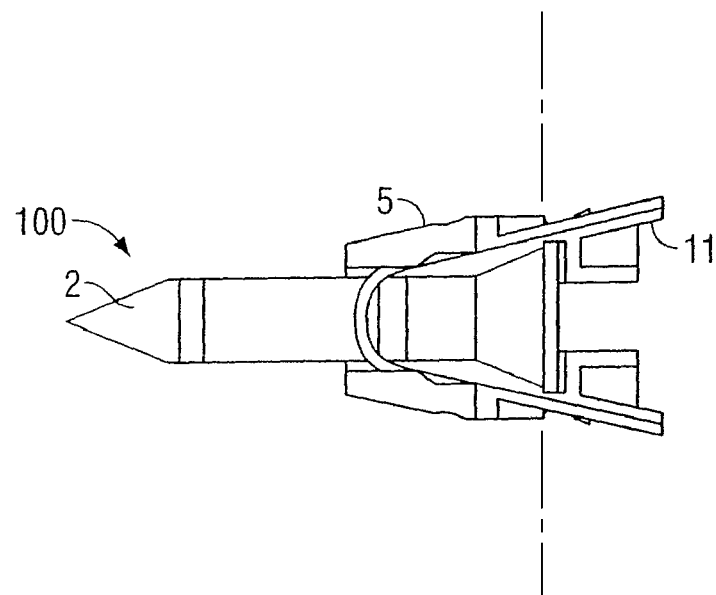
FIG. 5 shows a cross section view of an embodiment of the present invention including an final configuration of the locking body, collar, and a suture.

FIGS. 4 and 5 show cross sectional views of suture anchor 100 with a suture 11 threaded there through. In FIG. 4, anchor collar 5 is substantially proximal to suture 11. This formation is the initial configuration prior to deployment or insertion of the suture anchor 100 into bone. Suture anchor collar 5 has a diameter of θ initially. FIG. 5 shows the anchor collar 5 in a substantially distal relationship with suture 11, which is the configuration after insertion and deployment of the suture anchor 100 into bone. As may be seen, suture anchor collar 5 now has a diameter of θ+δ. This expansion of the suture anchor collar 5 occurs when the locking body 75 is pushed through the suture anchor collar 5 as the suture anchor 100 is inserted into bone. As may be seen in FIG. 5, suture 11 is guided along the sides of locking body 75 and held taut by anchor collar 5. In a preferred embodiment, the final length of the suture anchor 100 following insertion may be equal to or less than 20 mm.

Figure 6:
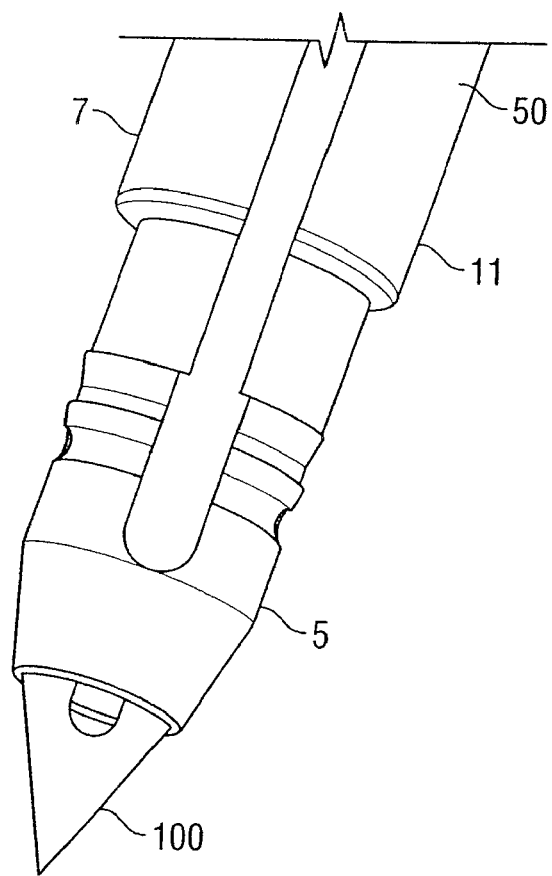
FIG. 6 shows another embodiment of the present invention with two sutures threaded through the eyelet of the locking body.

FIG. 6 shows a perspective view of suture anchor 100 attached to insertion tool 50. In FIG. 6, two sutures are seen threaded through suture anchor 100. The configuration shown in FIG. 6 is the initial configuration prior to insertion of the suture anchor 100 into bone.

Figure 7:
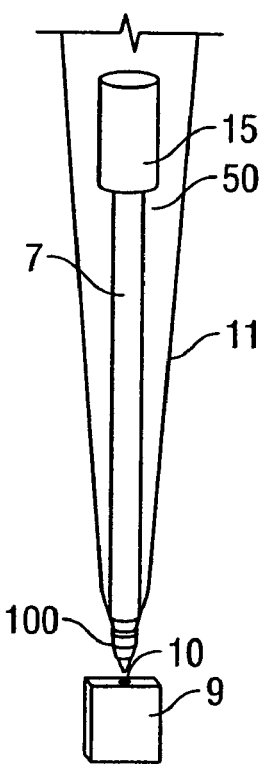
FIG. 7 shows a perspective view of an embodiment of the present invention including the installation instrument, suture anchor and collar.
Figure 8:
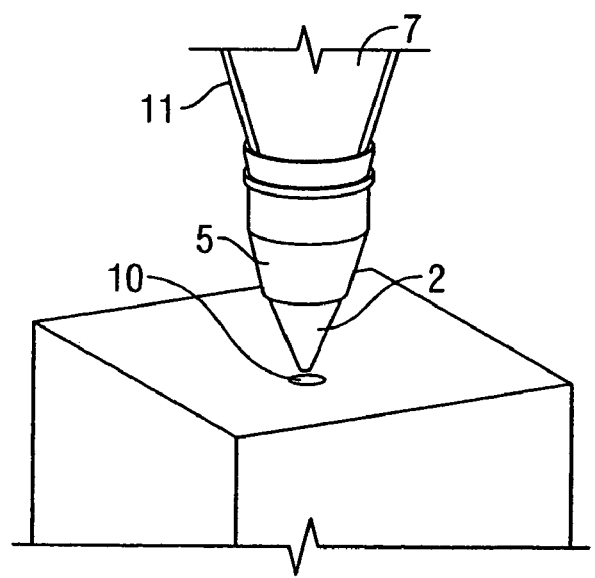
FIG. 8 shows an enlarged view of FIG. 7.

FIG. 7 shows a full view of the installation tool 50 with suture anchor 100 attached thereto. The installation tool 50 includes the cannula 7 discussed earlier and a cap 15 located on the proximal end of cannula 7. FIG. 7 also shows the installation tool 50 with the suture anchor 100 preparing to enter a pre-drilled hole 10 in a bone 9. FIG. 8 shows an enlarged view of FIG. 7.

Figure 9:
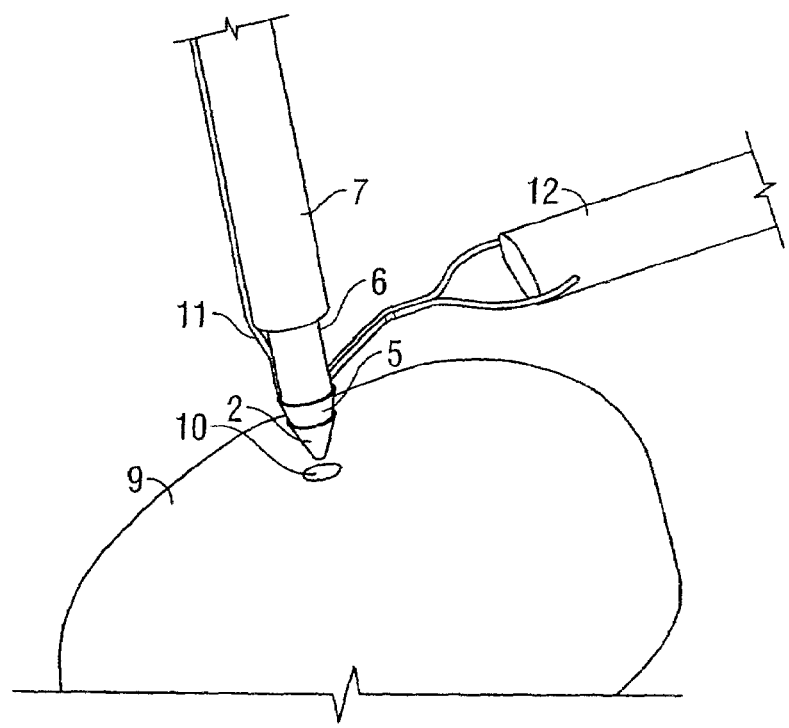
FIG. 9 shows a perspective view of an embodiment of the suture anchor about to be inserted into bone at a repair site.

FIG. 9 also shows a preferred embodiment of the suture anchor of the present invention prior to insertion. A suture 11 has been threaded through soft tissue 12 and the eyelet 3 in the locking body 75, which is, in part, covered by anchor collar holder 6. If the surgeon wishes, the suture 11 may be woven through the soft tissue 12, thereby allowing for more secure fixation and greater repair strength. The collar 5 is distal to the suture 11 and the eyelet 3, and proximal to the distal head 2 of the locking body 75. The anchor collar holder 6 of the installation tool is adjacent to the proximal end of the anchor collar 5. The suture anchor is positioned to be pushed into pre-drilled hole 10 in bone 9, to which the soft tissue 12 will be attached. The bone hole 10 is preferably drilled such that the hole reaches through the cortical bone layer to the cancellous bone layer. The hole 9 should be slightly smaller than the width of the distal head 2 of the locking body 75 and the anchor collar 5. This will allow both the locking body 75 and the anchor collar 5 to gain purchase within the bone hole 10. Preferably, the suture anchor 100 will ultimately be inserted through bone hole 10 and come to rest in the cancellous bone layer.

In the embodiment of FIG. 9, there are two lines of suture (both ends of the same strand of suture) that are being passed through the locking body 75. This provides secure fixation of the soft tissue to the suture anchor. In other embodiments, the number of lines of suture that are passed through the central anchor post may be increased, or decreased, depending upon the particular repair being performed.

Figure 10:
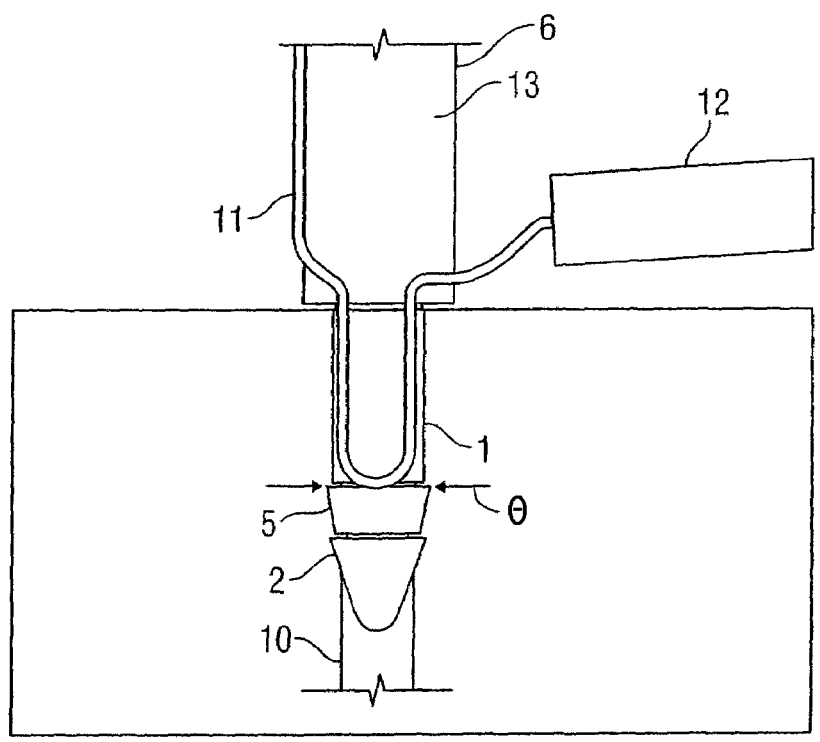
FIG. 10 shows a cross-sectional view of an embodiment of the suture anchor of the present invention after being initially inserted into bone at a repair site.

FIG. 10 shows, in cross-section, a preferred embodiment of the suture anchor of the present invention after being initially inserted into a hole 10 in the bone 9. The suture threads 11 pass through the locking body 75 and are pulled into the hole 9 in the bone 10. The distal head 2 of the locking body 75 and the anchor collar 5 are securely positioned within the hole 10 in the bone 9. As the suture anchor is positioned in the hole 10 in the bone 9, the soft tissue 12 is pulled to the repair site.

Figure 11:
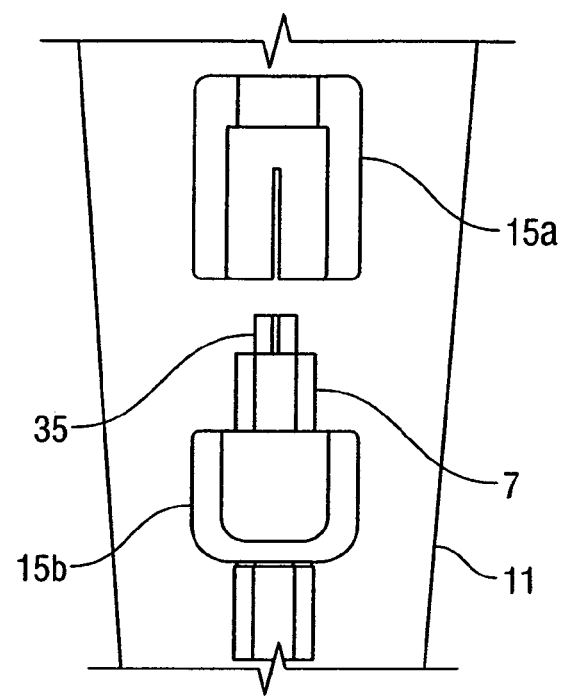
FIG. 11 shows a perspective view of the proximal end of the installation instrument.

FIG. 11 shows an enlarged view of the proximal end of the installation tool 50. After insertion of the suture anchor 100 into the pre-drilled bone hole 9, a portion of the cap 15*a* is removed to reveal push rod 35 Push rod 35 is then pushed by any known means such that the proximal end of the push rod 35 is flush with the proximal end of cannula 7. By pushing push rod 35, the locking body 75 is pushed farther into bone 9. As the anchor collar 5 moves, it engages and locks the suture and locking body 75 into place.

Figure 12:
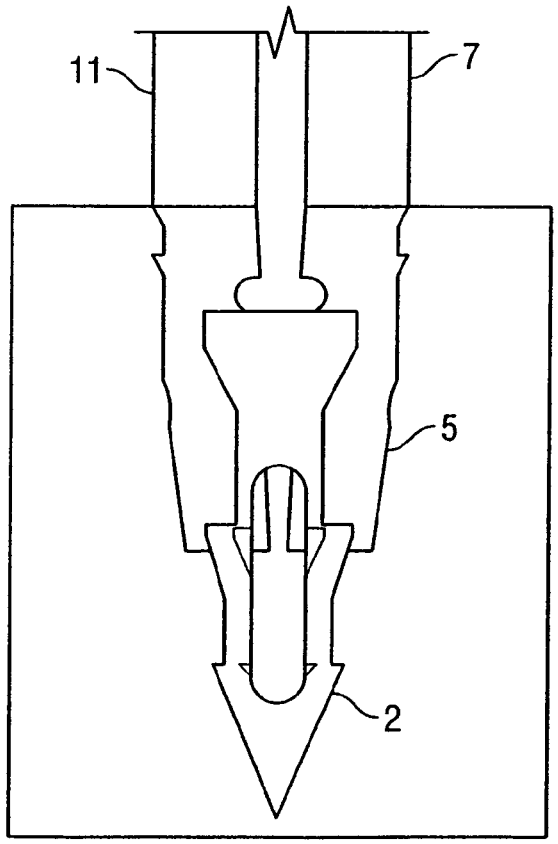
FIG. 12 shows a cross-sectional view of an embodiment of the suture anchor of the present invention after the locking body has been pushed further into the bone.
Figure 13:
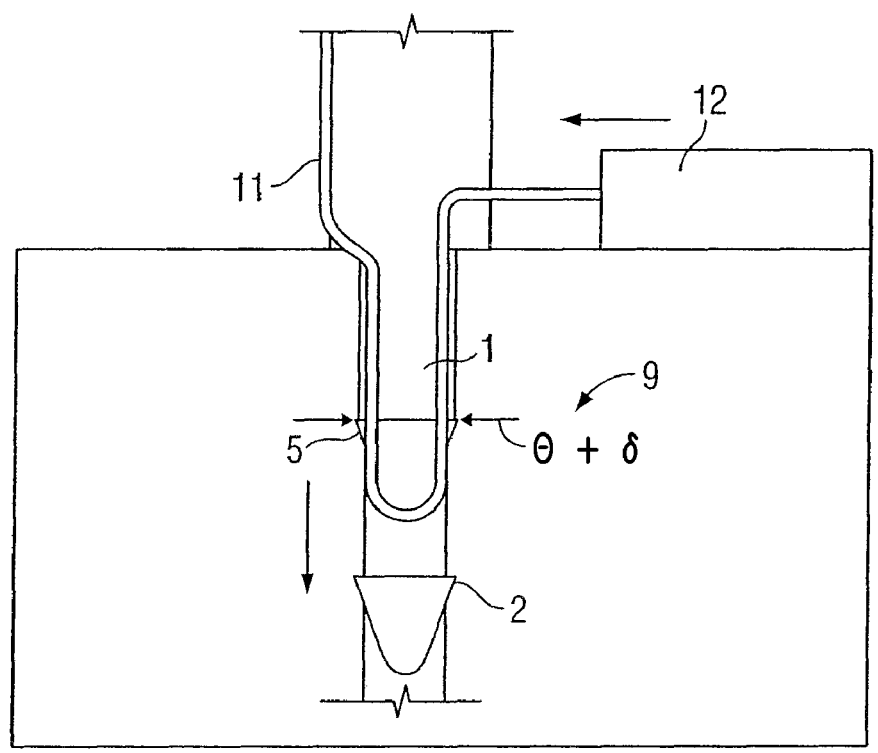
FIG. 13 shows a cross-sectional view of an embodiment of the suture anchor of the present invention after the locking body has been pushed further into the bone.

FIGS. 12 and 13 show, in cross-section, a preferred embodiment of the suture anchor 100 of the present invention after the locking body 75 has been fully inserted into the hole 10 in the bone 9. The push rod 35 of the installation tool has pushed the locking body 75 farther into the hole 10 in the bone 9 in the distal direction. The push rod 35 does not push down on the proximal end of the anchor collar 5, and the anchor collar is not pushed further into the hole 10 in the bone 9. As a result, the locking body 75 moves distally relative to the anchor collar 5, thereby expanding the anchor collar 5 to a diameter of θ+δ. The eyelet 3 moves from its location on the proximal side of the anchor collar 5 to a position that is distal to the anchor collar 5. The suture threads 11 are pulled farther into the hole 10 in the bone 9 and the soft tissue 12 is drawn closer to the bone anchor. The suture threads 11 are now drawn under the anchor collar 5 and are secured by the anchor collar 5. The suture threads 11 in FIG. 13 may no longer be pulled through the locking body 75, because they are held tight by the anchor collar 5. The distal head 2 of the locking body 75 is now securely positioned near the bottom of the hole 10 in the bone 9.

In a preferred embodiment, the hole 10 in the bone 9 may be drilled with a tapered drill, so that the distal end of the hole 10 is narrower than its opening. This serves to further prevent the anchor collar 5 from moving distally when the push rod 35 pushes the locking body 75 further into the hole 10. Additionally, the narrowness of the hole 10 allows the distal head 2 to more securely attach to the bone 9 when the suture anchor 100 is fully installed.

In yet another preferred embodiment, the anchor collar 5 will deform slightly into an oval shape as the push rod 35 pushes the locking body 75 further into the hole 10 and pulls the suture threads 11 under the anchor collar 5. As the suture threads 11 travel under the anchor collar 5, the anchor collar will bow out slightly. This will even more firmly affix the anchor collar within the hole 10 in the bone 9, ensuring that the suture anchor will not easily pull out of the hole 10. A preferred pull-out strength for the suture anchor 100, ranges from approximately 125N to 300N.

Figure 14:
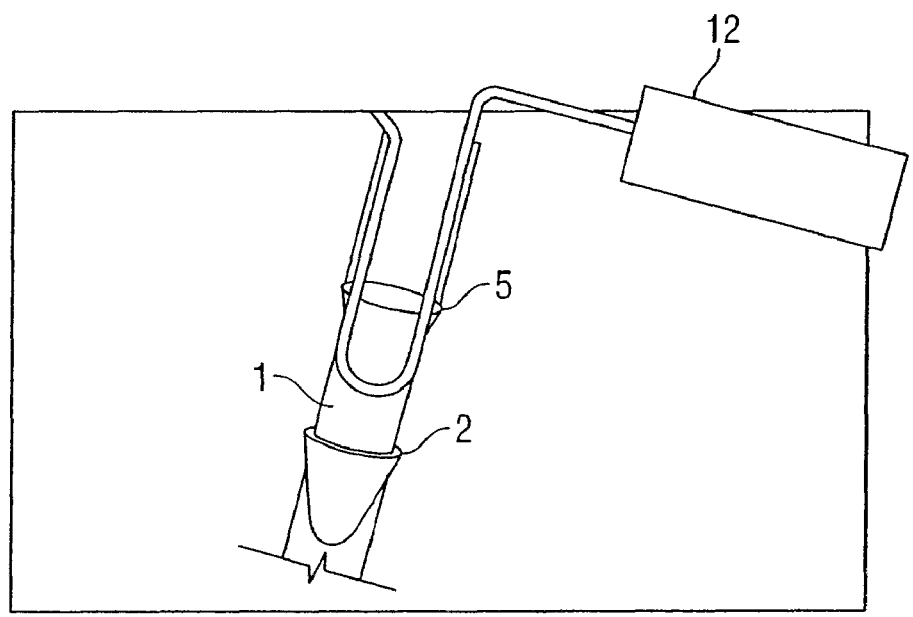
FIG. 14 shows a cross sectional view of an embodiment of the suture anchor of the present invention after insertion of the suture anchor has been completed.

FIG. 14 shows, in cross-section, a preferred embodiment of the suture anchor 100 of the present invention after the suture anchor has been installed. The installation tool 50 has been removed and the suture threads 11 that have been pulled through the locking body 75 have been cut at the opening of the hole 10. In a preferred method of insertion, the proximal end of the locking body 75 is positioned below the opening of the hole 10 at the surface of the bone 9 in the cancellous bone layer. This leaves little or no material protruding from the bone 9, which decreases the risk of foreign material causing irritation or damage within the joint.

Figure 15:
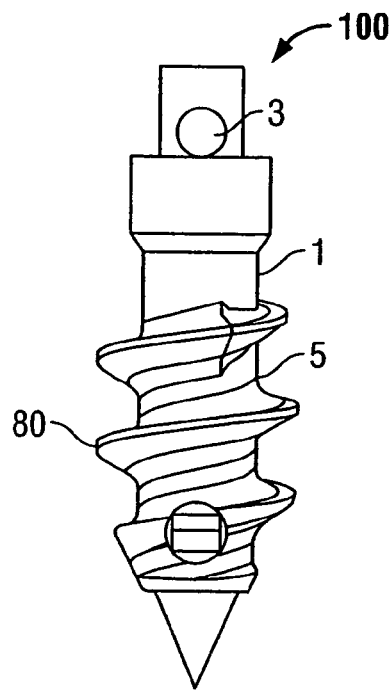
FIG. 15 shows a perspective view of another embodiment of the suture anchor of the present invention in an initial configuration, having a anchor collar including screw threads.
Figure 16:
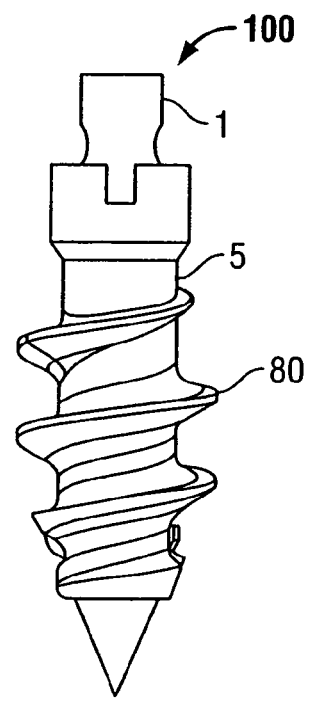
FIG. 16 shows another perspective view of the suture anchor of claim 15.
Figure 17:
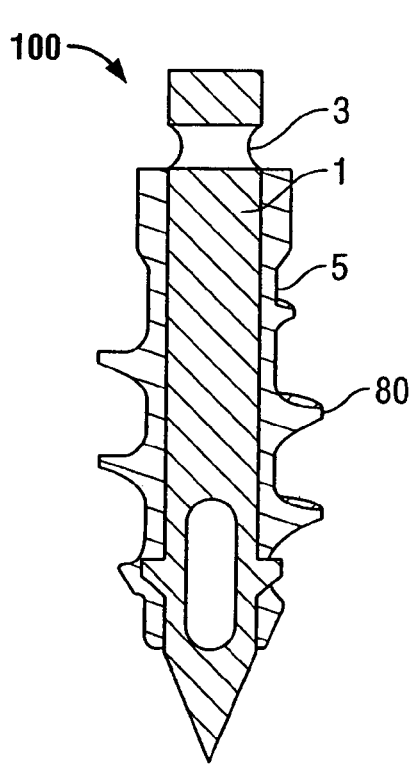
FIG. 17 shows a cross sectional view of the suture anchor of FIGS. 15 and 16.
Figure 18:
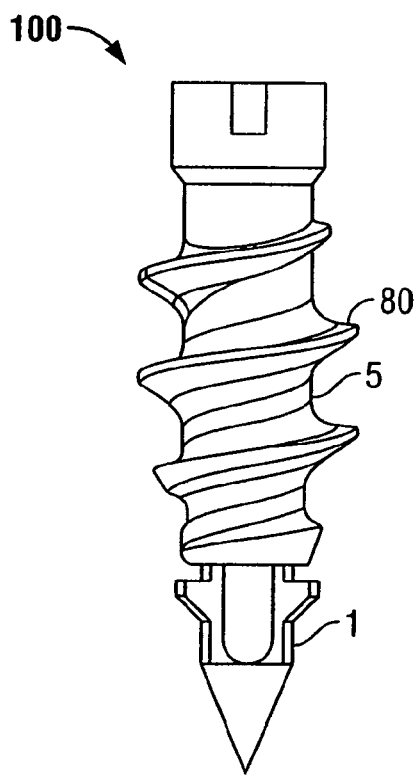
FIG. 18 shows a perspective view of the suture anchor of FIG. 15 in a final configuration.
Figure 19:
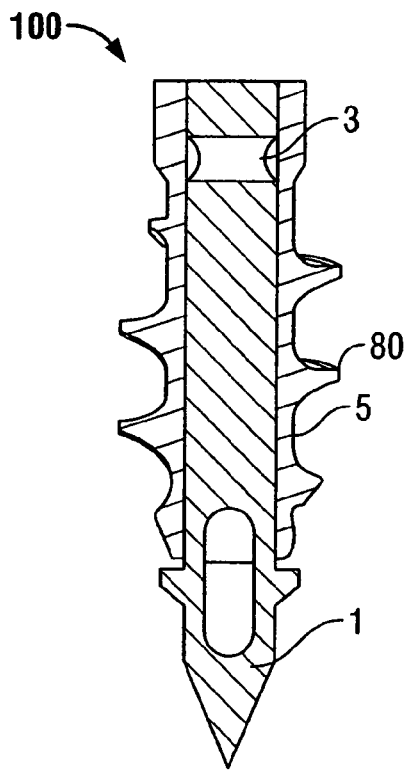
FIG. 19 shows a cross sectional view of FIG. 18.
Figure 20:
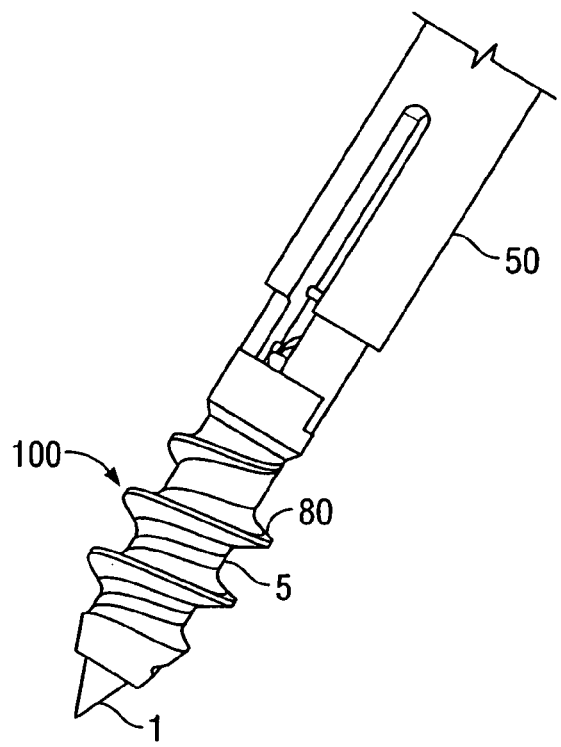
FIG. 20 shows a perspective view of the suture anchor of FIG. 15 attached to an installation tool.
Figure 21:
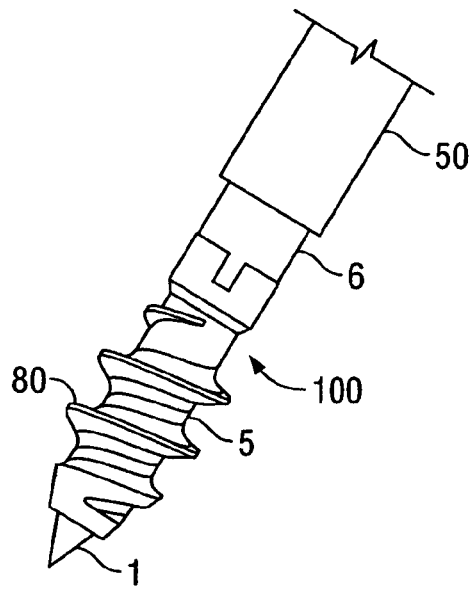
FIG. 21 shows another perspective view of FIG. 20.
Figure 22:
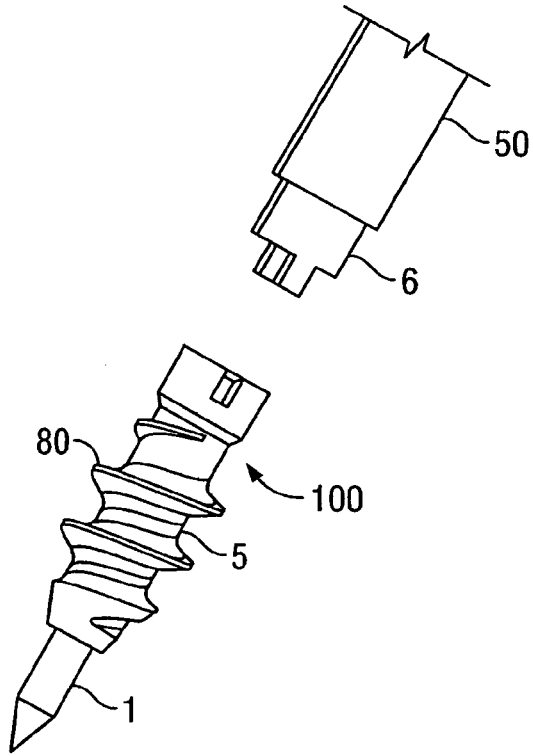
FIG. 22 shows a perspective view of the suture anchor of FIG. 18 disengaged from an installation tool.

FIGS. 15-22 show another embodiment of the suture anchor of the present invention. In this embodiment, the suture anchor 100 includes an anchor collar 5 that has at least one screw thread 80 as a protuberance and likely will have more than one. FIGS. 15-17 show the initial configuration of the suture anchor 100, where the anchor collar 5 is proximal to the locking body. FIGS. 18-19 show the final configuration after the locking body 1 has been pushed into bone relative to the anchor collar 5. FIGS. 20-22 also show initial and final configurations of the suture anchor 100 with an installation tool 50.

In a preferred procedure for using a suture anchor of the present invention, the surgeon attaches suture thread of his choosing through the soft tissue to be repaired in a manner of his choosing. The suture thread is then drawn through the eyelet in the locking body. The collar is positioned proximal to the eyelet before the suture is drawn through the eyelet. The suture anchor is then inserted partially into the bone through a pre-drilled hole, such that the collar and the locking body are secured within the bone. This may be done by pushing the suture anchor into the pre-drilled hole or screwing the suture anchor into the bone. At this time, the surgeon may tension the suture through the eyelet as he wishes, so that the soft tissue is pulled into approximation with the repair site. When the soft tissue is properly positioned and the suture has been properly tensioned, the surgeon taps the locking body further into the bone. As the locking body moves further into the bone, the collar remains in its initial position, lodged in the bone. Thus, the locking body moves distally with respect to the collar. The eyelet, through which the suture is threaded, moves under and past the collar, thereby drawing the suture under the collar. The collar holds the suture securely, and prevents the soft tissue from pulling away from the repair site. Thus, the suture anchor securely holds the soft tissue in place without requiring the surgeon to knot the suture.

After the description above of the present invention and certain specific embodiments thereof, it will be readily apparent to those skilled in the art that many variations and modifications may be made to the present invention without departing from the spirit and scope thereof.

What we claim is:

1. A method for attaching tissue to bone comprising:
   (a) providing a suture anchor comprising, a locking body comprising a central anchoring post, an eyelet configured to receive one or more suture threads, and at least one protuberance for securing said central anchoring post in bone; and a collar movably engaged with said central anchoring post, said collar having a hole therethrough for receiving said central anchoring post and having an exterior surface comprising at least one protuberance for securing said collar in bone, wherein said collar is configured to lock one or more suture threads between said collar and said locking body;
   (b) attaching suture thread to said tissue;
   (c) positioning the ends of said suture thread through said eyelet, with said collar located distally to said eyelet;
   (d) inserting said suture anchor into a pre-drilled hole in said bone while keeping said collar positioned distally to said eyelet;
   (e) positioning said tissue by applying force to said ends of said suture thread; and
   (f) further inserting said locking body into said hole in said bone so that said collar is located proximally to said eyelet, with said suture thread locked between said collar and said central anchoring post.

2. The method of claim 1, wherein said pre-drilled hole in said bone is tapered.

3. The method of claim 1, wherein inserting said suture anchor includes pushing said suture anchor into said pre-drilled hole.

4. The method of claim 1, wherein inserting said suture anchor includes screwing said suture anchor into said pre-drilled hole.

* * * * *